US006113900A

United States Patent
Strom

[11] Patent Number: 6,113,900
[45] Date of Patent: *Sep. 5, 2000

[54] USE OF IL-2 RECEPTOR-TARGETED THERAPEUTICS TO INHIBIT ALLOGRAFT REJECTION AND TREAT AUTOIMMUNE DISORDERS

[75] Inventor: Terry B. Strom, Brookline, Mass.

[73] Assignee: The Beth Israel Hospital Association, Boston, Mass.

[*] Notice: This patent is subject to a terminal disclaimer.

[21] Appl. No.: 08/975,563

[22] Filed: Nov. 21, 1997

Related U.S. Application Data

[63] Continuation of application No. 08/761,975, Dec. 11, 1996, Pat. No. 5,916,559, which is a continuation of application No. 08/469,538, Jun. 6, 1995, Pat. No. 5,607,675, which is a continuation of application No. 08/275,010, Jul. 8, 1994, Pat. No. 5,510,105, which is a division of application No. 07/842,463, Feb. 27, 1992, Pat. No. 5,336,489, which is a continuation of application No. 07/692,830, Apr. 26, 1991, abandoned, which is a continuation of application No. 07/492,616, Mar. 12, 1990, abandoned, which is a continuation of application No. 06/772,893, Sep. 5, 1985, Pat. No. 5,011,684.

[51] Int. Cl.[7] .......................... A61K 38/20; A61K 39/395
[52] U.S. Cl. .................... 424/144.1; 424/182.1; 424/183.1; 424/85.2; 424/85.1; 424/145.1; 424/144.1; 424/134.1; 424/173.1; 424/197.11; 424/195.11; 424/154.1
[58] Field of Search ............... 424/182.1, 183.1, 424/85.2, 85.1, 145.1, 144.1, 134.1, 173.1, 197.11, 195.11, 154.1; 514/2, 8

[56] References Cited

U.S. PATENT DOCUMENTS

| | | |
|---|---|---|
| 4,359,457 | 11/1982 | Neville et al. . |
| 4,388,309 | 6/1983 | Fabricius . |
| 4,440,747 | 4/1984 | Neville . |
| 4,443,427 | 4/1984 | Reinherz et al. . |
| 4,489,710 | 12/1984 | Spitler . |
| 4,520,226 | 5/1985 | Neville et al. . |
| 4,545,985 | 10/1985 | Pastan . |
| 4,550,086 | 10/1985 | Reinherz et al. . |
| 4,675,382 | 6/1987 | Murphy . |
| 4,677,061 | 6/1987 | Rose et al. . |
| 4,908,433 | 3/1990 | Mertelsmann . |
| 4,946,674 | 8/1990 | von Eichborn et al. . |
| 5,011,684 | 4/1991 | Strom . |
| 5,080,898 | 1/1992 | Murphy . |
| 5,336,489 | 8/1994 | Strom . |
| 5,510,105 | 4/1996 | Strom . |
| 5,587,162 | 12/1996 | Strom . |
| 5,607,675 | 3/1997 | Strom . |
| 5,674,494 | 10/1997 | Strom . |
| 5,916,559 | 6/1999 | Strom ................................. 424/144.1 |

FOREIGN PATENT DOCUMENTS

| | | |
|---|---|---|
| 091539 | 10/1983 | European Pat. Off. . |
| 118977 | 9/1984 | European Pat. Off. . |
| 119621 | 9/1984 | European Pat. Off. . |
| 140109 | 5/1985 | European Pat. Off. . |
| 89/01340 | 2/1989 | WIPO . |

*Primary Examiner*—David L. Fitzgerald
*Attorney, Agent, or Firm*—Lerner, David, Littenberg, Krumholz & Mentlik, LLP

[57] ABSTRACT

Methods of inhibiting allograft rejection and of inhibiting B lymphocyte-mediated autoimmune diseases are provided. The methods involve the use of agents specific for the IL-2 receptor, such as monoclonal antibodies or IL-2, optionally linked to a cytotoxin. Administration of the agents inhibits the proliferation of lymphocytes expressing the IL-2 receptor and thus mitigates unwanted immune responses.

48 Claims, 1 Drawing Sheet

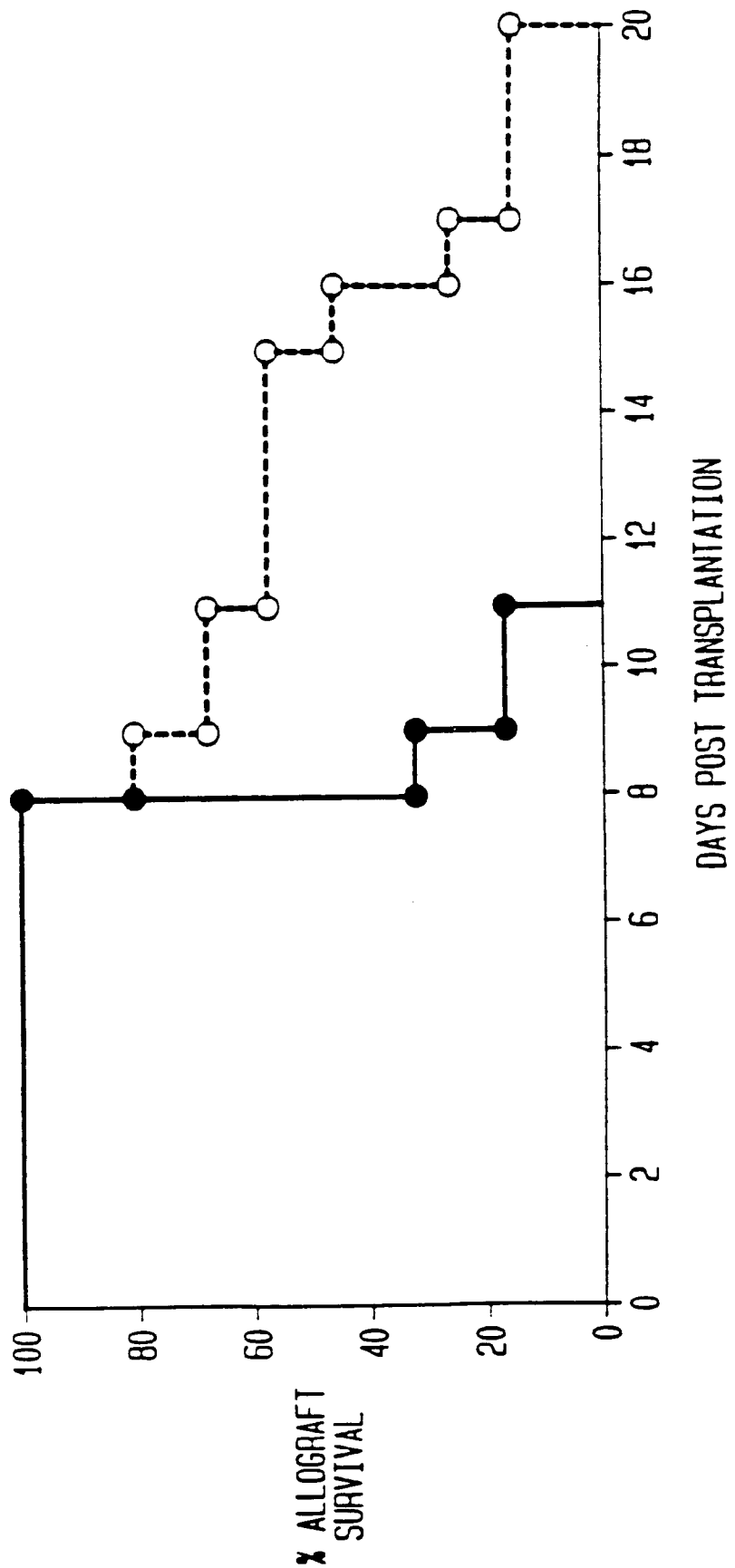

USE OF IL-2 RECEPTOR-TARGETED THERAPEUTICS TO INHIBIT ALLOGRAFT REJECTION AND TREAT AUTOIMMUNE DISORDERS

CROSS REFERENCE TO RELATED APPLICATIONS

This application is a continuation of application Ser. No. 08/761,975, filed Dec. 11, 1996, now U.S. Pat. No. 5,916,559; which is a continuation of application Ser. No. 08/469,538 filed Jun. 6, 1995, now U.S. Pat. No. 5,607,675; which is a continuation of application Ser. No. 08/275,010 filed Jul. 8, 1994, now U.S. Pat. No. 5,510,105; which is a divisional of application Ser. No. 07/842,463 filed Feb. 27, 1992, now U.S. Pat. No. 5,336,489; which is a continuation of application Ser. No. 07/692,830, filed Apr. 26, 1991, now abandoned; which is a continuation of application Ser. No. 07/492,616 filed Mar. 12, 1990, now abandoned; which is a continuation of application Ser. No. 06/772,893, filed Sep. 5, 1985, now U.S. Pat. No. 5,011,684.

STATEMENT AS TO FEDERALLY SPONSORED RESEARCH

Funding for the work described herein was provided by the federal government, which has certain rights in the invention.

BACKGROUND OF THE INVENTION

This invention relates to the lysis of unwanted, non-malignant cells, e.g., lymphocytes involved in the rejection of allografts such as transplanted organs.

Allograft rejection is an immune response, involving activated T-lymphocytes. Currently used immunosuppressive protocols designed to inhibit rejection involve the administration of drugs such as azathioprine, cyclosporine, and corticosteroids, all of which cause toxic side-effects to non-lymphoid tissues. The recent development of pan-T-lymphocyte monoclonal antibodies represents an important refinement in therapy, since only T-lymphocytes are targeted by the administration of such antibodies. However, this therapy has the disadvantage of destroying, along with the T-lymphocytes involved in allograft rejection, those required for normal immune surveillance.

SUMMARY OF THE INVENTION

In general, the invention features a method of lysing unwanted, non-malignant cells in a mammal, which cells have on their surfaces a receptor for a growth factor; the method substance characterized in that it has specific affinity for the growth factor receptor and has the ability to effect lysis of the cells. (As used herein, "malignant" cells refers to cancerous cells, e.g., primary or metastatic solid tumor cells, or leukemia cells; the non-malignant cells targeted according to the invention are unwanted cells which are not cancerous. "Growth factor" refers to a substance which, when taken into a cell after binding to a growth factor receptor on the surface of the cell, facilitates proliferation of the cell. "Specific affinity" refers to the ability of a substance to bind virtually exclusively to a particular growth factor receptor, e.g., the interleukin-2 ("IL-2") receptor, and not to other cell surface receptor proteins, e.g., insulin receptors.)

In preferred embodiments, the unwanted cells are lymphocytes, i.e., T-lymphocytes or B-lymphocytes, and the growth factor receptor-specific substance includes either an antibody (preferably a monoclonal antibody of the lytic IgG or IgM isotypes) or the growth factor itself (or a receptor-specific analog hereof) linked to a cytotoxin, e.g., diphtheria toxin or ricin, via either a convalent linkage such as a disulfide linkage or, more preferably, via a peptide linkage.

The unwanted, non-malignant cells most preferred to be lysed by the method of the invention are T-lymphocytes, which are the cell type primarily responsible for causing rejection of allografts (e.g., transplanted organs such as the heart). T-lymphocytes (killer and helper) respond to allografts by undergoing a proliferative burst characterized by the transitory presence on the T-lymphocyte surfaces of IL-2 receptors. Killing these cells by the administration, during the proliferative burst, of a lytic, IL-2 receptor-specific substance inhibits allograft rejection, and also advantageously fails to adversely affect other cells (including resting or long-term memory T-lymphocytes needed for fighting infections), since these other cells do not bear IL-2 receptors and are therefore not recognized by the IL-2 receptor-specific substance. In addition, cell lysis according to the invention is efficient because the IL-2 receptor binds to IL-2 receptor-specific substances so that the cytotoxin, if one is involved, is internalized in a way which results in cell death.

Where the lytic substance is an antibody of the complement-fixing IgG or IgM isotypes, it is not necessary that the antibody compete with IL-2 for the IL-2 receptor; i.e., the antibody can be one which binds to the receptor in a way which permits IL-2 to bind as well. Competitive binding is, however, important, for non-lytic IL-2 receptor-specific substances, as is discussed below.

The concept that allograft rejection can be inhibited by taking advantage of the proliferative burst of attacking T-lymphocytes which is characterized by the transient presence of IL-2 receptors on the surfaces of the T-lymphocytes can also form the basis for inhibiting allograft rejection using an IL-2 receptor-specific substance which, by virtue of its binding to the IL-2 receptors of the T-lymphocytes which would otherwise attack the allograft, impairs their ability to cause rejection of the allograft, but does not lyse them via complement fixation. Such substances, (e.g., non-complement fixing IgA antibodies), to be effective, must compete with IL-2 for the IL-2 receptor, so that their administration will prevent IL-2 from binding to the T-lymphocytes.

This preventing of the binding of IL-2 to T-lymphocytes can result in several important phenomena which contribute to rejection inhibition. First, the T-lymphocytes, newly activated by the presence of the allograft, fail to proliferate, and eventually die, due to the lack of the essential anabolic stimulus IL-2. In addition, the T-lymphocytes, deprived of IL-2, fail to release at least three lymphokines which play important roles in organ rejection. One of these, gamma interferon, normally activates allograft-attacking macrophages, and also stimulates the allograft to produce additional antigen, marking the allograft for more vigorous attack by the immune system. A second of these lymphokines is B-cell differentiation factor II, which ordinarily would stimulate the differentiation of B-cells, which in turn would produce allograft-attacking antibodies. A third lymphokine is IL-3, a hematopoietic stem cell growth factor also believed to play an important role in allograft rejection.

The method of the invention inhibits allograft rejection in a manner which does not cause general immune suppression, with its resulting risk of life-threatening infections. In addition, the method spares donor-specific T suppressor cells, which can thus proliferate and aid in prolonging allograft survival. Furthermore, antibodies do not need to be tailored to individual patients; a single antibody can be used as a universal allograft rejection inhibiting agent for every donor-recipient combination. In addition, therapy need not be continuous following the allograft, but can be discontinued after a course of treatment.

Other features and advantages of the invention will be apparent from the following description of the preferred embodiments thereof, and from the claims.

DESCRIPTION OF THE PREFERRED EMBODIMENTS

The drawing will first be described.

DRAWING

In the drawing, the FIGURE is a graph showing skin allograft survival following treatment with an antibody according to the invention (open circles with dashed line, n=9) and untreated controls (closed circles with solid line, n=7).

ANTIBODY THERAPY

One embodiment of the invention employs, as the IL-2 receptor-specific substance, an antibody (preferably monoclonal) which is specific for the IL-2 receptor on T-lymphocytes and which is preferably capable of effecting in vivo lysis of T-lymphocytes to whose IL-2 receptors it binds. Antibodies specific for the IL-2 receptor on T-lymphocytes can be made using standard techniques, or can be purchased, e.g., from Becton Dickenson Company (mouse-human monoclonal anti-IL-2 receptor antibodies, packaged in azide, which would need to be removed prior to use). The antibody can be used alone, or it can be coupled to a toxin to increase its lytic capacity. The antibody can be monoclonal or polyclonal, and can be derived from any suitable animals. Where the antibody is monoclonal and the mammal being treated is human, mouse-human anti-IL-2 receptor antibodies are preferred.

Production and initial screening of monoclonal antibodies to yield those specific for the IL-2 receptor can be carried out as described in Uchiyama et al. (1981) J. Immunol. 126 (4), 1393; this method, briefly, is as follows. Human cultured T-lymphocytes are injected into mammals, e.g., mice, and the spleens of the immunized animals are removed and the spleen cells separated and then fused with immortal cells, e.g., mouse or human myeloma cells, to form hybridomas.

The antibody-containing supernatants from the cultured supernatants are then screened for those specific for the IL-2 receptor, using a complement-dependent cytotoxicity test, as follows. Human T-lymphocytes and EBV transformed B-lymphocytes are labeled with $^{51}$Cr sodium chromate and used as target cells; these cells are incubated with hybridoma culture supernatants and with complement, and then the supernatants are collected and counted with a gamma counter. Those supernatants exhibiting toxicity against activated T-lymphocytes, but not resting T- or B-lymphocytes, are selected, and then subjected to a further screening step to select those supernatants containing antibody which precipitates (i.e., is specifically reactive with) the 50 kilodalton glycoprotein IL-2 receptor (described in detail in Leonard et al. (1983) P.N.A.S. USA 80, 6957). The desired anti-IL-2 receptor antibody is purified from the supernatants using conventional methods.

Graft rejection inhibition employing anti-IL-2 receptor monoclonal antibodies has been carried out using two different mammalian species, mice and rats, as described below.

Mice

Animals and Operative Techniques

Inbred male mice weighing 20–25 grams of strains C57B1/10, B10.BR, and B10.AKM (Jackson Laboratory, Bar Harbor, Me.) were used throughout. These strains are completely mismatched for the H-2 locus, but share the same genetic background.

Vascularized, heterotopic heart allografts were performed as originally described by Corry et al. Transplantation (1973) 16, 343. The aorta was anastomosed to the abdominal aorta, and the pulmonary artery to the adjacent vena cava using standard microvascular techniques with 10-0 nylon suture (Ethicon, Inc., Somerville, N.J.) under 20× magnification. With completion of the anastomoses and warming of the heart with Ringer's lactate solution at 37° C., normal sinus rhythm was resumed. Function of the transplant heart was assessed by daily palpation of ventricular contractions through the abdominal wall. Rejection was defined as the cessation of all mycardial contractions, which was confirmed at laparotomy under ether anesthesia.

To perform skin grafts, full thickness tail skin was removed from a donor sacrificed by cervical dislocation. The recipient was anesthetized with ether, shaven, and a graft bed prepared on the posterior flank by removing a 0.5×0.5 cm portion of skin, with care taken not to injure the underlying panniculus or its blood vessels. The graft was shaped to fit the graft bed, positioned, and covered with baseline gauze. A bandage was then wrapped circumferentially around the chest to protect the graft. The grafts were inspected daily beginning on day 6 or 7, and considered rejected when greater than 50% of the epithelium was non-viable.

Preparation and Administration of Monoclonal Antibody

The monoclonal antibody employed was antibody M7/20, which is described in Gaulton et al. (1985) Clin. Immunol. and Immunopath. M7/20 is a monoclonal rat anti-mouse x, u, Ig antibody specific for the IL-2 receptor. M7/20 was purified from the culture supernatants of cells grown in serum free media (Hanna Labs, Berkeley, Calif.). Supernatants were precipitated with 40–50% saturated ammonium sulfate, dialyzed, passed over DEAE Affi-Gel Blue (Bio-Rad, Richmond, Va.) in 20 mM NaCl, and the eluate fractionated on Sephadex G-200 (Pharmacia, Piscataway, N.J.), run in 20 mM Tris (pH 7.2), 250 mM NaCl, 0.5% n-butanol. Antibody purity was assessed by SDS-Page gel electrophoresis. There was also employed a control monoclonal antibody, RA3.2C2, not specific for the IL-2 receptor. The hybridoma producing RA3-2C2, which binds to pre-B cells and to some mature B cells, was obtained from the American Type Culture Collection (Rockville, Md.), and the antibody purified by the procedure described above for M7/20.

Both antibodies were diluted to a final concentration of 25 μg/ml in phosphate buffered saline. Treated recipients of heart or skin allografts received 0.2 ml (5 μg) by intraperitoneal injection daily for 10 days, usually beginning the day of transplant. In a small number of heart graft recipients, the onset of treatment was delayed until day 3 or 6, then given for a total of 10 daily doses.

Histology

Separate groups of treated and untreated C57B1/10 recipients of B10.BR heart allografts were sacrificed at intervals post-transplant for histologic studies. Hearts were removed from two animals in each group at days 3, 6, and 9 following transplantation, fixed in formalin, sectioned, and stained with hematoxylin and eosin.

Results

The results, given in Table I, below, demonstrate the ability of M7/20 to prevent rejection of vascularized heart allografts in two strain combinations of inbred mice control C57B1/10 heart allografts in untreated B10.AKM recipients were rejected with a median survival of 8 days. However, when treatment with M7/20 was begun on the day of transplant and continued for 10 days at a dose of 5 μg daily, 4 of 6 grafts survived indefinitely (>90 days), with two rejecting at 20 and 31 days. This survival is significantly longer than control (p<.01). Similar results were obtained in C57B1/10 recipients of B10.BR heart allografts. Control grafts were rejected at 10–20 days, while treated grafts were not rejected until 20, 27, 34, 38 days, with two grafts functioning for more than sixty days (p<.01). Treatment with RA3-2C2 did not prolong graft survival.

Table 1. The effect of M7/20 on survival of murine heart allografts.

| Recipient | Donor   | Treatment      | Allograft Survival in Days |
|-----------|---------|----------------|----------------------------|
| B10.AKM   | C57B1/10| none           | 8,8,8,8,16,29              |
| B10.AKM   | C57B1/10| M7/20[a]       | 20,31,>90,>90,>90,>90      |
| B10.AKM   | C57B1/10| RA3-2C2[a]     | 6,9,9,10,>90               |
| C57B1/10  | B10.BR  | none           | 9,10,10,10,14,16,20,20     |
| C57B1/10  | B10.BR  | M7/20[a]       | 20,27,34,38,>60,>60        |
| C57B1/10  | B10.BR  | M7/20,day3[b]  | 11,15,18,>30               |
| C57B1/10  | B10.BR  | m7/20,day6[c]  | 19,>30,>30                 |

[a]5 μg i.p. daily for 10 days
[b]5 μg i.p. daily for 10 days beginning day 3
[c]5 Mg i.p. daily for 10 days beginning day 6

The effect of M7/20 on graft rejection was confirmed histologically in separate groups of C57B/10 recipients of B10.BR heart allografts sacrificed at intervals following transplantation. By three days post-transplant control grafts were heavily infiltrated by mononuclear cells. Treatment with M7/20 prevented this graft infiltration. Treated grafts at days 6 and 9 had some areas of mononuclear cell infiltration, but markedly less than in control grafts. Both treated and control grafts contained considerable myocyte necrosis, evident even at three days post-transplant. This necrosis appeared unrelated to the rejection process, and may represent ischemic damage sustained during transplantation.

The efficacy of M7/20 in reversing established rejection was examined in a small number of C57B1/10 recipients of BLO.BR allografts (Table 10). In four animals the onset of treatment was delayed until day 3, by which time rejection was ongoing, and continued through day 12. Three grafts were rejected on days 11, 15, and 18, while the fourth was still functioning at 30 days. When treatment was given on days 6–15, one graft was rejected at 19 days, while two were still functioning at 30 days.

The influence of M7/20 on skin allograft survival was studied in the same strain combinations used for heart allografts. As seen in the Figure, when C57B1/10 skin was placed on B10.AKM recipients, M7/20 at a dose of 5 μ daily for 10 days significantly prolonged graft survival when compared with controls (p<.01). However, none of the skin grafts survived indefinitely. M7/20 was ineffective in prolonging the survival of B10.BR skin on C57B1/10 recipients.

Rats

Animals and Operative Techniques

Inbred male rats weighing 200–250 g were used throughout (Microbiological Assoc., Walkersville, Md.). Unmodified Lewis rats acted as organ recipients and Lewis-Brown Norway F1 hybrids served as heart donors. Wistar Furth rats were used as heart donors for specificity studies.

Heterotopic cardiac grafts were anastomosed to the abdominal great vessels according to the method of Ono et al. (1969) J. Thorac. Cardiovasc. Surg. 57, 225. The size and ventricular activity were assessed daily by palpation through the recipient flank. Rejection was taken as the time of complete cessation of myocardial contractions.

Preparation and Administration of Monoclonal Antibody

A mouse anti-rat IgG, anti-IL-2 receptor monoclonal antibody was obtained from cultured hybridoma cells (designated ART 18) made according to the method of Kohler and Milstein (1975) Nature 256, 495, as modified by Lemke et al. (1978) Nature 271, 249, and described in detail in Osowa et al. (1983) J. Immunol. 30, 51 (the mice were primed with phorbol myristate activated rat T-lymphocytes). The antibody recognizes the rat 50-kilodalton glycoprotein IL-2 receptor molecule; binds to rat T-lymphoblasts at a rate of $7.5 \times 10^4$ binding sites per cell; does not bind to mature, resting T-lymphocytes; and does not affect the functioning of mouse T-lymphocytes not bearing IL-2 receptors.

Antibody (protein concentration 10 mg/ml, 5 mg/ml of pure antibody) was diluted in medium and administered to experimental animals intravenously at a dose of 25–300 ug of antibody/kg/day for 5 or 10 consecutive days. Alzet osmotic pumps (Model 2 ML1, Alza Corp., Palo Alto, Calif.) were inserted into the external jugular vein of some recipients to give a constant infusion of antibody (10.5 ul/hr for 10 days), as is described in further detail below.

Allograft recipients received anti-IL-2 receptor antibody therapy according to arbitrarily chosen doses and durations of treatment. Antibody administered intravenously in doses of 25, 100, or 300 ug/kg/day for 10 consecutive days beginning on the day of grafting increased the mean allograft survival (compared to the untreated 8-day survival rate) in a dose dependent fashion to MST±SD=13±1 days, 14±3 days, and 21±1 days, respectively. Limiting the period of treatment to the first five post-transplant days was less effective and resulted in a significant graft prolongation only when antibody was given at a dose of 300 ug/kg/day (14±2 days, p<0.005).

The efficacy of antibody therapy in reversing well established allograft rejection was also tested. Treatment was initated at 5 days after transplantation, at which time the grafts were grossly enlarged and heavily infiltrated with lymphocytes. Significantly, antibody therapy started day 5 after transplantation and continued for 5 days at a dose of 300 ug/kg/day improved allograft survival to 18±4 days, a result comparable to the effect produced by 10 consecutive injections. In addition, the dense cellular infiltrate noted histologically in acute rejection at day 5 had virtually disappeared after the antibody therapy. Intermittent antibody adminstration (5–9 and 15–19 days, with no treatment on days 10–14) extended graft survival even further, to 26–28 days, while lower antibody doses were ineffectual in reversing ongoing rejection.

To demonstrate that the results of antibody treatment were not unique to one strain combination, Wistar Furth rat recipients of Lewis cardiac grafts underwent antibody treatment (300 ug/kg/daily) for 10 days beginning the day of transplantation. Allograft survival was prolonged to 16±1 days.

In the next series of experiments, antibody was administered (300 ug/kg/day over ten days) intravenously in a constant infusion of 10.5 ul/hr using an Alzet osmotic pump. Such treatment was significantly less effective than the above-described "pulse" treatment in preventing rejection (graft survival=12–13 days, n=3, p<0.005).

Non-Competition with IL-2

The potentially offsetting effects of exogenously supplied anti-IL-2 receptor antibody IL-2 itself were studied in vivo within the microenvironment of unmodified graft recipients. As shown above, sole therapy with the antibody directed at the rat IL-2 receptor increases cardiac allograft survival to about 3 weeks. In contrast, it has been previously shown that a course of IL-2 accelerates immune responsiveness. To test the effects of the two together, the optimal doses of each (300 ug/kg of antibody and 100 ul of IL-2) were mixed and delivered in daily intravenous injections for a period of 10 days. Interestingly, this combined treatment produced the same effect as if antibody had been administered alone (graft survival=20±2 days, n=4), suggesting that an excess of IL-2 does not prevent in vivo binding of antibody to IL-2 receptor-bearing cells. Moreover, these results suggest that, in the case of this particular antibody, treatment prolongs engraftment by destroying IL-2 receptor positive cells rather than by pharmacological blocking of the IL-2 receptor.

Effect Antibody Therapy on T Suppressor Cells

Spleen cells were harvested at day 10 from heart grafted hosts after the dose regimen of anti-IL-2 receptor antibody had been completed, and transferred intravenously (40–50× $10^6$) into normal recipients which received test cardiac allografts 24 hrs later. Such adoptive transfer prolonged donor-specific (Lewis-Brown Norway F1 hybrids) but not third-party (Wistar Furth) test graft survival (15±1 days and 8±1 days, respectively, n=5, p<0.001). Thus, potent antigen specific suppressor, but little alloaggressive activity, was demonstrated in animals maintaining well-functioning cardiac allografts following antibody therapy. In other words, the antibody advantageously lysed most (but not all) receptor-bearing T-lymphocytes, but spared the T-suppressor cells, which are important in inhibiting rejection.

Human Dosage and Administration

Dosages of anti-rejection substances will vary, depending on factors such as whether or not the substance is lytic, and the condition of the patient. Generally, lytic monoclonal anti-IL-2 receptor antibodies will be administered in a series (e.g., two to fifteen more preferably 5 to ten intravenous doses, given, e.g., once or twice daily or every two or three days, or in regular courses interrupted by periods of cessation of treatment), begun on the day of the transplant; each dose preferably will be in the range of about 50–1000 ug/kg. In some instances, treatment initiation can be delayed one or more days following the allograft, since therapy not only can prevent rejection, but can reverse it as well.

Other Embodiments

Other embodiments are within the following claims. For example, the cell-lysing substance can be specific for a growth factor receptor other than the IL-2 receptor, provided that the growth factor is present primarily on the surfaces of unwanted target cells during a proliferative burst, and is not found on the surfaces of normal cells to an extent which would result in their lysis to an unacceptable extent upon administration of the substance. In the case of the IL-2 receptor, the target cells can be unwanted B-lymphocytes, which, like T-lymphocytes, bear IL-2 receptors on their surfaces during proliferative bursts associated, e.g., with acute stages of autoimmune diseases such as systemic lupus erythmatosus. In addition, acute stages of autoimmune diseases such as multiple sclerosis apparently, like allograft rejection, involve T-lymphocytes which undergo proliferative bursts associated with the transient appearance of IL-2 receptors, and patients with such an acute disease can be treated by administering an effective amount of an IL-2 receptor-specific affinity substance capable of lysing the lymphocytes or interfering with IL-2 binding to them. The lytic substance, rather than an antibody, can be the growth factor itself (which is highly specific for the growth factor receptor) linked to a toxin, e.g., ricin or diphtheria toxin.

What is claimed is:

1. A method of inhibiting rejection of an allograft in a mammal, comprising administering to said mammal an IL-2 receptor specific antibody in an amount effective to inhibit proliferation of IL-2 receptor bearing T-lymphocytes which induce rejection of the allograft.

2. The method of claim 1, wherein said IL-2 receptor specific antibody is administered on the day of said allograft.

3. The method of claim 1, wherein said IL-2 receptor specific antibody kills said T-lymphocytes.

4. The method of claim 1, where said IL-2 receptor specific antibody is a complement fixing antibody.

5. The method of claim 1, wherein said IL-2 receptor specific antibody is a monoclonal antibody.

6. The method of claim 1, wherein said allograft is a skin allograft.

7. The method of claim 1, wherein said allograft is a transplanted organ.

8. The method of claim 7, wherein said transplanted organ is a heart.

9. The method of claim 1 wherein said IL-2 receptor specific antibody is a non-complement fixing antibody.

10. A method of inhibiting T-lymphocyte-induced rejection of an allograft in a mammal, comprising administering to said mammal a cytotoxin linked to an IL-2 receptor-specific substance in an amount effective to inhibit rejection of the allograft.

11. The method of claim 10, wherein said cytotoxin linked to an IL-2 receptor bearing substance is administered on the day of said allograft.

12. The method of claim 10, wherein said cytotoxin is diphtheria toxin.

13. The method of claim 12 wherein said IL-2 receptor specific substance is IL-2.

14. The method of claim 10, wherein said cytotoxin is ricin.

15. The method of claim 10, wherein said IL-2 receptor specific substance is, IL-2.

16. The method of claim 10, wherein said IL-2 receptor-specific substance is an antibody.

17. The method of claim 16, wherein said antibody is a monoclonal antibody.

18. The method of claim 16, wherein said allograft is a skin allograft.

19. The method of claim 10, wherein said allograft is a transplanted organ.

20. The method of claim 19, wherein said transplanted organ is a heart.

21. A method of treating a mammal suffering from an autoimmune disease, acute stages of which are characterized by a proliferative burst of IL-2 receptor bearing B lymphocytes, comprising administering to said mammal an IL-2 receptor specific antibody in an amount effective to inhibit or reduce the proliferative burst of the IL-2 receptor bearing lymphocytes.

22. The method of claim 21, wherein the disease is lupus.

23. The method of claim 21 wherein said IL-2 receptor specific antibody is administered during a proliferative burst of said IL-2 receptor bearing lymphocytes.

24. The method of claim 21 wherein said antibody is a monoclonal antibody.

25. The method of claim 21 wherein said antibody is a complement fixing antibody.

26. The method of claim 21 wherein said IL-2 receptor specific antibody is a non-complement fixing antibody.

27. A method of treating a mammal suffering from an autoimmune disease, acute stages of which are characterized by a proliferative burst of IL-2 receptor bearing B lymphocytes, comprising administering to said mammal a cytotoxin linked to an IL-2 receptor specific substance in an amount effective to inhibit or reduce the proliferative burst of the IL-2 receptor bearing lymphocytes.

28. The method of claim 27, wherein the disease is lupus.

29. The method of claim 27 wherein said cytotoxin linked to an IL-2 receptor specific substance is administered during a proliferative burst of said IL-2 receptor bearing lymphocytes.

30. The method of claim 27 wherein said cytotoxin is diphtheria toxin.

31. The method of claim 27 wherein said IL-2 receptor specific substance is IL-2.

32. The method of claim 27 wherein said cytotoxin is ricin.

33. The method of claim 27 wherein said IL-2 receptor specific substance is IL-2.

34. The method of claim 27 wherein said IL-2 receptor-specific substance is an antibody.

35. The method of claim 34 wherein said antibody is a monoclonal antibody.

36. A method of treating a mammal having an autoimmune disease, acute stages of which are characterized by a proliferative burst of IL-2 receptor bearing B lymphocytes, comprising administering to said mammal an IL-2 receptor specific antibody in an amount effective to treat the disease.

37. A method according to claim 36, wherein the disease is lupus.

38. The method of claim 37 wherein the antibody is a monoclonal antibody.

39. The method of claim 37 wherein the antibody is a complement fixing antibody.

40. The method of claim 37 wherein said IL-2 receptor specific antibody is a non-complement fixing antibody.

41. A method of treating a mammal having an autoimmune disease, acute stages of which are characterized by a proliferative burst of IL-2 receptor bearing B lymphocytes, comprising administering to said mammal a cytotoxin linked to an IL-2 receptor specific substance in an amount effective to treat the disease.

42. A method according to claim 41, wherein the disease is lupus.

43. The method of claim 42 wherein said cytotoxin is diphtheria toxin.

44. The method of claim 43 wherein said IL-2 receptor specific substance is IL-2.

45. The method of claim 42 wherein said cytotoxin is ricin.

46. The method of claim 42 wherein said IL-2 receptor specific substance is IL-2.

47. The method of claim 42 wherein said IL-2 receptor-specific substance is an antibody.

48. The method of claim 47 wherein said antibody is a monoclonal antibody.

* * * * *

UNITED STATES PATENT AND TRADEMARK OFFICE
CERTIFICATE OF CORRECTION

PATENT NO.  : 6,113,900
DATED       : September 5, 2000
INVENTOR(S) : Strom

It is certified that error appears in the above-identified patent and that said Letters Patent is hereby corrected as shown below:

Column 9,
Line 36, "27" should read -- 30 --.

Signed and Sealed this

Second Day of October, 2001

Attest:

NICHOLAS P. GODICI
*Attesting Officer*     *Acting Director of the United States Patent and Trademark Office*